United States Patent
Bollas et al.

(10) Patent No.: US 10,495,547 B2
(45) Date of Patent: Dec. 3, 2019

(54) PLATE-FIN HEAT EXCHANGER FOULING IDENTIFICATION

(71) Applicant: HAMILTON SUNDSTRAND CORPORATION, Windsor Locks, CT (US)

(72) Inventors: George M. Bollas, Tolland, CT (US); Kyle Palmer, Willington, CT (US); Dilip Prasad, North Granby, CT (US); Clas A. Jacobson, Tolland, CT (US); John M. Maljanian, Jr., Farmington, CT (US); Richard A. Poisson, Avon, CT (US); Young K. Park, Simsbury, CT (US)

(73) Assignee: HAMILTON SUNDSTRAND CORPORATION, Windsor Locks, CT (US)

( * ) Notice: Subject to any disclaimer, the term of this patent is extended or adjusted under 35 U.S.C. 154(b) by 242 days.

(21) Appl. No.: 15/168,741

(22) Filed: May 31, 2016

(65) Prior Publication Data

US 2016/0356677 A1    Dec. 8, 2016

Related U.S. Application Data

(60) Provisional application No. 62/172,486, filed on Jun. 8, 2015.

(51) Int. Cl.
*G01M 99/00* (2011.01)
*G05B 23/02* (2006.01)
(Continued)

(52) U.S. Cl.
CPC .......... *G01M 99/005* (2013.01); *B64D 13/08* (2013.01); *G05B 23/0254* (2013.01);
(Continued)

(58) Field of Classification Search
None
See application file for complete search history.

(56) References Cited

U.S. PATENT DOCUMENTS 5,086,622 A     2/1992   Warner
7,827,006 B2 *  11/2010  Miller ............. G05B 23/024
                                          702/183
(Continued)

FOREIGN PATENT DOCUMENTS

EP     2682835 A2    1/2014

OTHER PUBLICATIONS

Lalot et al., "Detection of Fouling in a Heat Exchanger Using a Recursive Subspace Identification Algorithm" The 19th International Symposium on Transport Phenomena Aug. 17-21, 2008, Reykjavik, Iceland.*

(Continued)

*Primary Examiner* — John C Kuan
(74) *Attorney, Agent, or Firm* — Cantor Colburn LLP

(57) ABSTRACT

A computer-implemented method for designing a built-in test is described. The method includes receiving, via a processor, a subsystem model including system parameters for a heat exchanger, wherein each of the system parameters includes a sensor variance; determining, via the processor, a test design vector based on one or more of the system parameters; and designing, via the processor, the built-in test based on the test design vector.

9 Claims, 8 Drawing Sheets

(51) Int. Cl.
*G06F 17/50* (2006.01)
*B64D 13/08* (2006.01)
*G01N 17/00* (2006.01)
*B64D 13/06* (2006.01)
*G06F 11/00* (2006.01)

(52) U.S. Cl.
CPC ........ *G06F 11/008* (2013.01); *G06F 17/5009* (2013.01); *B64D 2013/0603* (2013.01); *F28F 2200/00* (2013.01); *G01N 17/008* (2013.01)

(56) References Cited

U.S. PATENT DOCUMENTS

| | | | | |
|---|---|---|---|---|
| 8,762,106 | B2* | 6/2014 | Miller | G05B 17/02 702/179 |
| 9,804,607 | B1* | 10/2017 | Coleman | G05D 7/00 |
| 2014/0008035 | A1* | 1/2014 | Patankar | F28F 27/00 165/11.1 |
| 2016/0297538 | A1* | 10/2016 | Soriano | B64D 37/00 |
| 2016/0305865 | A1* | 10/2016 | Silva | G01N 17/008 |
| 2016/0320291 | A1* | 11/2016 | Najjar | G01N 17/008 |
| 2017/0061295 | A1* | 3/2017 | Horabin | G05B 23/0235 |

OTHER PUBLICATIONS

Jonsson et al., "Use of extended Kalman filtering in detecting fouling in heat exchangers" International Journal of Heat and Mass Transfer 50 (2007) 2643-2655.*
Kyle A. Palmer et al., "Optimal Design of Tests for Heat Exchanger Fouling Identification", Applied Thermal Engineering 95, 2016, pp. 382-393.
European Search Report for EP Application No. 16173593.1 dated Dec. 7, 2016; 13 pages.
Gudmundsson et al.; "Comparison of Fouling Detection Methods Using Experimental Data"; Proceedings of international conference on Heat exchanger Fouling and cleaning; Jun. 14, 2014, pp. 429-436.
Ma et al.; "Fault Diagnosis for the Heat Exchanger of the Aircraft Environmental Control System Based on the Strong Tracking Filter"; PLOS ONE, vol. 10, No. 3, Mar. 30, 2015, pp. 1-11.
Shah et al.; "On-Line Fouling Detection of Aircraft Environmental Control System Cross Flow Heat Exchanger"; Mechatronics and Automation, ICMA 2009 International Conference; Aug. 12, 2009, pp. 2940-2945.
F. Delmotte, M. Dambrine, S. Delrot, S. Lalot, Fouling detection in a heat exchanger: A polynomial fuzzy observer approach, Control Engineering Practice. 21 (2013) 1386-1395.
G. Franceschini, S. Macchietto, Model-based design of experiments for parameter precision: State of the art, Chemical Engineering Science. 63 (2008) 4846-4872.
G.R. Jonsson, S. Lalot, O.P. Palsson, B. Desmet, Use of extended Kalman filtering in detecting fouling in heat exchangers, International Journal of Heat and Mass Transfer. 50 (2007) 2643-2655.
H. Al-Asaad, M. Shringi, On-line built-in self-test for operational faults, 2000 IEEE Autotestcon Proceedings. IEEE Systems Readiness Technology Conference. Future Sustainment for Military Aerospace (Cat. No. 00CH37057). (2000) 168-174.
I. Pérez-Grande, T.J. Leo, Optimization of a commercial aircraft environmental control system, Applied Thermal Engineering. 22 (2002) 1885-1904.
L. Shang, G. Liu, Heat exchanger fouling detection in a simulated aircraft engine bleed air temperature control system, in: IEEE/ASME International Conference on Advanced Intelligent Mechatronics, AIM, 2010: pp. 774-778.
M. Rodriguez-Fernandez, S. Kucherenko, C. Pantelides, N. Shah, Optimal experimental design based on global sensitivity analysis, in: 17th European Symposium on Computer Aided Process Engineering, 2007: pp. 1-6.
O. Gudmundsson, Detection of fouling in heat exchangers. Thesis., University of Iceland, 2008.
O. Gudmundsson, S. Lalot, J. Thorsen, Comparison of Fouling Detection Methods, in: Proceedings of International Conference on Heat Exchanger Fouling and Cleaning, 2013: pp. 429-436.
R.K. Shah, D.P. Sekuli, Fundamentals of Heat Exchanger Design, John Wiley & Sons, Inc., Hoboken, NJ, USA, 2003.
S. Körkel, E. Kostina, H.G. Bock, J.P. Schlöder, Numerical methods for optimal control problems in design of robust optimal experiments for nonlinear dynamic processes, Optimization Methods and Software. 19 (2004) 327-338.
S. Lalot, H. Pálsson, Detection of fouling in a cross-flow heat exchanger using a neural network based technique, International Journal of Thermal Sciences. 49 (2010) 675-679.
S. Le Digabel, Algorithm 909: {NOMAD}: Nonlinear optimization with the {MADS} algorithm, ACM Transactions on Mathematical Software. 37 (2011) 44:1-44:15.
S. Shah, G. Liu, D.R. Greatrix, On-line fouling detection of aircraft environmental control system cross flow heat exchanger, in: 2009 IEEE International Conference on Mechatronics and Automation, ICMA 2009, 2009: pp. 2940-2945.
S. Wright, G. Andrews, H. Sabir, A review of heat exchanger fouling in the context of aircraft air-conditioning systems, and the potential for electrostatic filtering, Applied Thermal Engineering. 29 (2009) 2596-2609.
S. Zubair, A. Sheikh, M. Younas, M. Budair, A risk based heat exchanger analysis subject to fouling Part I☐: Performance evaluation, Energy. 25 (2000) 427-443.
T. Skoglund, K.-E.E. Årzén, P. Dejmek, Dynamic object-oriented heat exchanger models for simulation of fluid property transitions, International Journal of Heat and Mass Transfer. 49 (2006) 2291-2303.

* cited by examiner

| Flow Condition | Nominal Setting |
| --- | --- |
| $T_h$ (°C) | 175 |
| $T_a$ (°C) | 15 |
| $\dot{m}_h$ (kg/s) | 0.30 |
| $\dot{m}_a$ (kg/s) | 1.00 |
| $p_h$ (kPa) | 250 |
| $p_a$ (kPa) | 100 |

Table 1. Conditions applied in the ECS heat exchanger case studies of fouling estimation

FIG. 2

| IBIT settings φ | Nominal $T_g = 175°C, n_s = 1, \tau = 300s$ | | | Optimal $T_g = [100°C, 250°C], t_s = [20s, 280s],$ $n_s = 2, \tau = 300s$ | | |
|---|---|---|---|---|---|---|
| | $\dot{m}_{cl}$ (kg/s) | $\dot{m}_{bc}$ (kg/s × 10³) | $R_f$ (m²K/W × 10⁵) | $\dot{m}_{cl}$ (kg/s) | $\dot{m}_{bc}$ (kg/s × 10³) | $R_f$ (m²K/W × 10⁵) |
| Ram flow rate only | 1.00 ± 0.003 | – | 5.94 ± 0.42 | 1.00 ± 0.003 | – | 6.27 ± 0.34 |
| Bleed flow rate only | – | 3.00 ± 0.010 | 5.90 ± 0.64 | – | 3.00 ± 0.007 | 6.12 ± 0.47 |
| Ram and Bleed flow rates | 1.00 ± 1.36 | 3.00 ± 4.12 | 5.91 ± 16.4 | 1.00 ± 0.010 | 3.00 ± 0.023 | 6.12 ± 1.05 |

Table 2. Estimated values and 95% confidence intervals of mass flow rates and thermal fouling resistance

FIG. 4

| Uncertain Condition | Nominal | Optimal | True values |
|---|---|---|---|
| $R_f$ (m²K/W × 10³) | 5.44 ± 133.5 | 6.50 ± 0.98 | 6.20 |
| $w_{a,p}$ (× 10⁵) | 1.03 ± 65.50 | 1.13 ± 0.33 | 1.20 |
| $T_c$ (°C) | 15.85 ± 54.45 | 15.05 ± 0.33 | 15.00 |
| $\dot{m}_a$ (kg/s) | 1.03 ± 1.65 | 1.00 ± 0.008 | 1.00 |

Table 3. Estimated values and 95% confidence intervals of uncertain heat exchanger inlets and fouling at nominal and optimal settings

FIG. 5

PLATE-FIN HEAT EXCHANGER FOULING IDENTIFICATION

BACKGROUND

The present disclosure relates to active fault detection and isolation of dynamical systems, and more specifically, to plate-fin heat exchanger fouling identification.

An objective of an aircraft environmental control system (ECS) is to provide fresh air at appropriate conditions for the passengers and crew, while performing secondary heating and cooling to various aircraft components. ECSs are required to control the temperature of hot "bleed" air stream after compression. Cross-flow plate-fin heat exchangers are typically used in ECSs because of their small weight and volume relative to their heat transfer efficiency. FIG. 1 depicts a conventional (reference) aircraft ECS piping and instrumentation diagram. The ECS primary heat exchanger 2 uses ambient ram air 4 as the cold fluid side to decrease the temperature of the compressed bleed stream. As a result, aircraft operations expose the ECS, and in particular its cold side, to fouling from contaminants such as sand, dust, and salt.

Fouling in aircraft ECSs is most often caused by deposition of dust particles suspended in the inlet airflow. Particulate accumulation is a function of air flow rate, concentration of contaminants, and system temperature and pressure. The accumulation of contaminants on the ECS heat exchanger surface significantly reduces its heat transfer efficiency and performance over time while also increasing pressure drop, leading to significant costs from maintenance and component failures.

SUMMARY

According to an embodiment of the present invention, a computer-implemented method for designing a built-in test is described. The method includes receiving, via a processor, a subsystem model including system parameters for a heat exchanger, wherein each of the system parameters includes a sensor variance; determining, via the processor, a test design vector based on one or more of the system parameters; and designing, via the processor, the built-in test based on the test design vector.

According to other embodiments, a system for designing a built-in test is described. The system may include at least one sensor configured for sensing one or more system variables of a heat exchanger; and a processor configured to receive a subsystem model including system parameters for the heat exchanger, where each of the system parameters includes a sensor variance; determine a test design vector based on one or more of the system parameters and allowable input variance; and design the built-in test based on the test design vector.

According to yet other embodiments, a computer program product for designing a built-in test is described. The computer program product includes a computer readable storage medium having program instructions embodied therewith, where the computer readable storage medium is not a transitory signal per se. The program instructions are executable by a processor operatively connected to at least one sensor to cause the processor to perform a method. The method includes receiving, via the processor, a subsystem model including system parameters for a heat exchanger, wherein each of the system parameters includes a sensor variance; determining, via the processor, a test design vector based on one or more of the system parameters; and designing, via the processor, the built-in test based on the test design vector.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 2 depicts a table showing estimated values and 95% confidence intervals of mass flow rates and thermal fouling resistance according to one embodiment.

FIG. 4 shows Table 2 indicating estimated values and 95% confidence intervals of mass flow rates and thermal fouling resistance;

FIG. 5 shows Table 3 indicating estimated values and 95% confidence intervals of uncertain heat exchanger inlets and fouling at nominal and optimal settings

DETAILED DESCRIPTION

Particulate fouling in plate fin heat exchangers of aircraft environmental control systems is a recurring issue in high foreign object debris environments. Heat exchanger fouling detection is important for aircraft maintenance scheduling and safe operation. Various embodiments and methods for offline fouling detection during aircraft ground handling are described hereafter, where the allowable variability range of admissible inputs may be wider. Some embodiments estimate heat exchanger inputs and input trajectories that maximize the identifiability of fouling. Some embodiments may build upon a cross-flow plate fin heat exchanger model of the inherent mass, energy and momentum balances. One embodiment is first validated against literature data and then it is used in a dynamic sensitivity analysis framework, in which sensitivities of the heat exchanger outputs with respect to fouling metrics are maximized and input trajectories that enhance identifiability of fouling are estimated.

Figure 1:
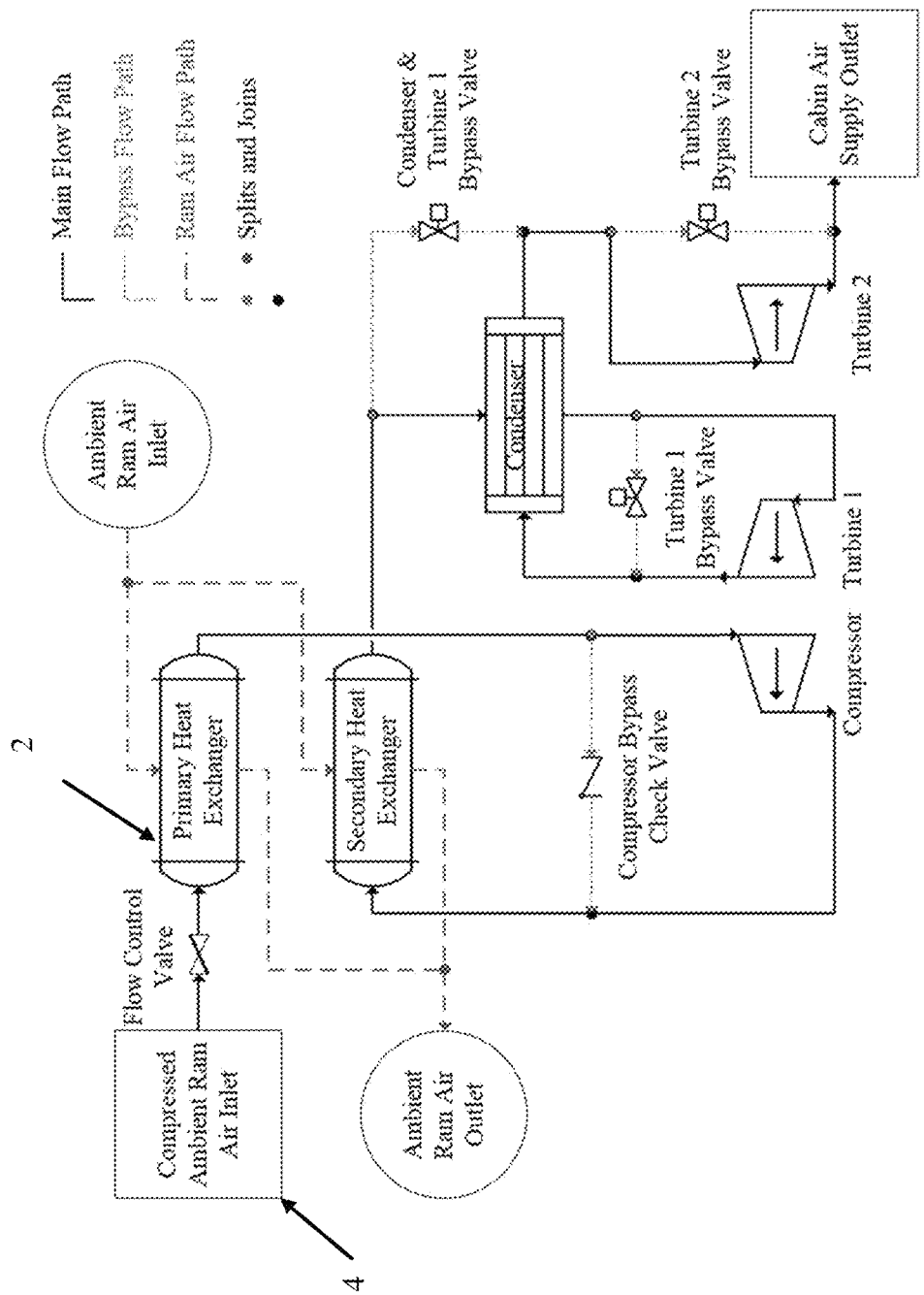
FIG. 1 depicts a conventional aircraft ECS piping and instrumentation diagram.

The primary objective of an aircraft environmental control system (ECS) is to provide fresh air at appropriate conditions for the passengers and crew, while performing secondary heating and cooling to various aircraft components. ECSs are required to control the temperature of hot "bleed" air stream after compression. Cross-flow plate-fin heat exchangers are typically used in ECSs because of their small weight and volume relative to their heat transfer efficiency. The ECS primary heat exchanger 2 (as depicted in FIG. 1) uses ambient ram air 4 as the cold fluid side to decrease the temperature of the compressed bleed stream. As a result, aircraft operations expose the ECS, and in particular its cold side, to fouling from contaminants such as sand, dust, and salt.

Fouling in aircraft ECSs is most often caused by deposition of dust particles suspended in the inlet airflow. Particulate accumulation is a function of air flow rate, concentration of contaminants, and system temperature and pressure. The accumulation of contaminants on the ECS heat exchanger surface may significantly reduce its heat transfer efficiency and performance over time while also increasing pressure drop, leading to significant costs from maintenance and component failures.

Fouling detection methods are the primary means for monitoring fouling and its impact on aircraft operation. Typically, online detection methods are applicable, to estimate system states and predict deviations in heat transfer effectiveness. Some conventional methods may use a Kalman filter, which may be designed for nonlinear state estimation and filtering of process and measurement noise. Other conventional methods may use a hybrid Kalman filter approach specifically for aircraft-related fouling detection that uses a continuous model combined with discrete-time measurements. Other approaches have used artificial neural networks to update weighted biases into system networked layers. Other conventional methods use weighted uncertainty into a heat exchanger model using a fuzzy polynomial approach. A black-box method was developed for performing model reduction using recursive subspace model identification. Other methods may use wavelet functions for fault detection by applying wavelet transforms onto continuous or discrete measurements to reduce output noise. All these detection methods treat fouling as a state that increases gradually over time. They are less effective at lower accumulation rates, as it becomes increasingly difficult to discern between system deviation, noise and uncertainty. Moreover, classic methods such as the Kalman filter are difficult to use during offline analysis, as the duration is very small compared to most online applications.

According to some embodiments for aircraft ECS heat exchanger fouling detection, when aircraft operates on the ground and prior to flight, a manually initiated built in test (hereafter "iBIT") may be used for fault detection. iBIT generally lasts minutes, whereas fouling typically occurs over hundreds of hours, a significant difference in time scales between the fouling process and the time available for its offline detection. This separation of time scales allows fouling affected properties, such as deposit thickness and thermal fouling resistance, to be treated as parameters. Correspondingly, an alternative approach for fouling detection can be applied on the basis of parameter estimation. Here, we propose a method that calculates a set of system inputs that minimize the uncertainty of the estimate of heat exchanger fouling from fault identification during iBIT. This technique is based on Optimal Experimental Design (OED) methods.

OED is a model-based method that combines a system model with measurements and their variance to decrease the uncertainty of estimated model parameters. The framework for OED is sometimes applied in precision-based estimation. Generally, the objective of design of experiments (DOE) is to minimize uncertainty and maximize the information that can be extracted from a series of experiments. Model-based DOE, or OED, relies on the explicit use of a mathematical model with uncertainty in its parameters, cast as an optimization problem that maximizes the information extractable from future experiments. Model-based experimental design can be applied to any system (linear, non-linear, steady-state or dynamic).

In some aspects, empirical correlations and model parameters are identified and known, and model input uncertainty is taken into consideration. The fouling detection method applies a framework inspired by OED to dynamic heat transfer analysis while considering operating constraints and uncertainty of a realistic iBIT. A cross-flow plate-fin heat exchanger model is first formulated to assess the effects of fouling and the implications of its detection. The plate fin heat exchanger model is validated with experimental data obtained from the literature. The iBIT OED problem is then formulated to explore sensitivities of the measured heat exchanger outputs with respect to fouling-related model parameters. System inputs are optimized to maximize these sensitivities, using the heat exchanger model employed in a D-optimal experimental design framework that reduces the joint confidence regions of the estimated parameters. Therefore, fouling is dissociated from system noise and input uncertainty in the heat exchanger, which is illustrated through a series of case studies.

The heat exchanger model was developed on the basis of mass, energy, and momentum conservation equations. Each stream of the plate fin heat exchanger may be considered to have a gradient solely along the direction of fluid flow, as the flow length is significantly larger than the fin spacing. The fluid flow can be considered one-dimensional along each fluid direction, whereas the crossflow plate walls that separate them may be modeled in two dimensions. The fins have uniform thickness and are assumed to have negligible thermal resistance compared to the plate walls. The fluids may be treated as ideal gases, and the thermal conductivity, dynamic viscosity, and specific heat capacity for each fluid can be calculated using known correlations. These properties may be considered to be unaffected by small foulant concentrations. A grid formulation may be used to discretize the heat exchanger into a series of sequential cells. The mass, energy and momentum balances can be therefore simplified to discrete axial profiles using the method of lines, with axial derivatives approximated by finite differences. The detailed mass, energy and momentum balances corresponding to the heat exchanger discretization can be found in Palmer et. al Appl. Th. Eng. 2016.

The mathematical problem of fouling identification in iBIT may be formulated based on conventional values and models for plate fin heat exchanger fouling identification. The input variables available in the real system, the measurements that are or can be available in an aircraft ECS, and realistic constraints for all the inputs and time scales, for the present explanation, may be considered known quantities derived and recorded by testing. It is noted that iBIT may be cast as a test (experiment) or series of tests that need to be performed for the identification of fouling and its isolation from other system uncertainties. The identification of the fault can be improved by maximizing the information that can be extracted from a test, relative to this fault. This information can be steady state or transient, which are both explored in the following. The model-based methodology discussed in the following embodiments may make use of the model previously described of which parametric sensitivities with respect to fouling indicators (parameters) are maximized in designing an optimal iBIT. Each optimal iBIT (which may consist of a series of tests) is then compared to a nominal iBIT comprising a set of tests performed at normal or standard ECS conditions.

According to some embodiments, heat exchanger fouling can be expressed as thermal fouling resistance, $R_f$, treated as a parameter during iBIT. Fouling resistance can affect the measured (at the system level) exit temperatures and pressures by reducing the overall heat transfer coefficient and decreasing the cross-sectional area of the heat exchanger, as detailed above. However, the same measured variables may be affected by other input or state variables, such as flow rates, inlet pressure, temperature, etc. Therefore, it is possible that uncertainty and noise in the inlet conditions or system states may be misinterpreted as fouling in certain situations. Overall, the objective of iBIT in this analysis is to estimate the thermal fouling resistance as accurately as possible in aircraft ECS with uncertainty in its states or inputs and other system parameters.

The uncertainties explored here can include conditions that affect heat transfer effectiveness. Specifically, the moisture content, $w_{H_2O}$ increases the fluid heat capacity (Eq. (3)) for gas heat exchangers, affecting the outlet temperature. The inlet pressure and mass flow in the bleed stream, $p_{hi}, \dot{m}_{hi}$, and ram stream, $p_{ci}, \dot{m}_{ci}$, control the density and velocity of each fluid, which impact heat transfer and pressure drop. The inlet ram temperature, $T_{ci}$, may have a significant effect on the exit temperature as shown in above. These system conditions or parameters are considered uncertain and are estimated along with the thermal fouling resistance through a series of case studies (detailed hereafter) to showcase the strengths and capabilities of disclosed embodiments. It should be noted that uncertainty is expressed in this work as a variance interval for each one of the variables considered. Depending on the level of confidence we have on the system measurements or on the accuracy of inferred variables, the intervals of each variable are expressed as wide or narrow bounds in their estimation. As such, even system inputs are considered unknown, and the level of accuracy in their value in the system is expressed by their upper and lower bounds. In summary, the unknown fouling resistance and uncertain inlet conditions can be compiled together as a vector of estimated system parameters and inputs:

$$\hat{\xi} = \hat{\theta} \cup \hat{u}[R_f, w_{H_2O}] \cup [\dot{m}_{hi}, \dot{m}_{ci}, p_{hi}, p_{ci}, T_{ci}] = [R_f, w_{H_2O}, \dot{m}_{hi}, \dot{m}_{ci}, p_{hi}, p_{ci}, T_{ci}] \quad (1)$$

Eq. (1) does not describe a complete iBIT input set for aircraft ECS. The bleed stream is typically controlled and conditioned by the bleed system before entering the primary heat exchanger. Here, the ECS iBIT problem is simplified by adjusting the inlet bleed temperature directly as input for optimal fouling detection, without considering the implications upstream to the bleed source. Moreover, the iBIT considered here changes the inlet bleed temperature in a series of discrete steps over time. The number of discrete step changes, $n_s$, and their duration, $t_s$, can be also optimized to find a balance between estimation confidence and complexity and duration of the design. The duration of each step may be constrained to a minimum of twenty seconds to allow for utilization of steady-state information when applicable. The initial conditions, $y^0$, can be optimized as well. In iBIT, optimality of $y^0$ corresponds to finding optimal system inputs for the initial system steady-state. The timespan of the iBIT analysis in an aircraft is relatively small to ensure all tests are completed within the aircraft ground handling time. Most iBITs run for less than ten minutes for aircraft diagnostics, so for this analysis the maximum test duration, $\tau$, may be set to five minutes. The inlet temperature, number of step changes, steps duration, and overall timespan are included in the test design vector, $\varphi$:

$$\varphi = [T_{hi}(t), t_s, n_s, y_0, \tau]^T \in \Phi \quad (2)$$

The variables of the test design vector of Eq. (2) may be restricted to a design space $\Phi$, assigning upper and lower bounds to each component. To formulate the iBIT design problem, within the allowable design space of the ECS, the model equations described above may be expressed as an implicit system of differential equations:

$$f(\dot{x}(t), x(t), u(t), \hat{\theta}, t) = 0, \quad (3)$$

where f is the system governing equations, x(t) is the system states (temperature and pressure), u(t) is the system inputs (inlet bleed temperature), and t is time. It may be assumed that sensors exist at the outlet bleed and ram channels to measure the exit temperatures and pressures, regardless of whether they exist in all ECSs. Estimates of the measured outputs, $\hat{y}(t)$, may then be expressed as:

$$\hat{y}(t) = h(x(t), \hat{\sigma}, u(t)) \quad (4)$$

The initial states $y^0$ can be arranged for the defined system as:

$$y^0 = \begin{cases} f(\dot{x}(t_0), x(t_0), u(t_0), \hat{\theta}, t_0) = 0, \\ \hat{y}(t_0) = h(x(t_0), \hat{\theta}, u(t_0)), \end{cases} \quad (5)$$

According to some embodiments, the optimal iBIT can provide maximum information on thermal fouling resistance, even at uncertain inlet conditions. This information is acquired through the sensitivities of measured outputs with respect to estimated values of for all sampling times within $\tau$. These sensitivities may be compiled into a series a of matrices, $Q_{r,s}$, for each output, $y_{r,s}$, and weighed by the experimental variance to produce the variance covariance matrix and Fisher information matrix:

$$V_{\hat{\theta}}(\hat{\theta}, \varphi) = H_{\hat{\theta}}^{-1}(\hat{\theta}, \varphi) = \left[\sum_r^{n_{resp}} \sum_s^{n_{resp}} \tilde{\sigma}_{rs} Q_r^T Q_s\right]^{-1} \quad (6)$$

where $\tilde{\sigma}_{rs}$ is the rs-th element of the experimental variance matrix, and $n_{resp}$ is the total number of measured outputs. The D-optimal design criterion may be chosen, for example, to minimize the correlation between estimated parameters from the extracted information, and thus isolate fouling from all other system uncertainty:

$$\varphi_D = \arg\min_{\varphi \in \Phi} \det(V_{\hat{\theta}}(\hat{\theta}, \varphi)) \quad (7)$$

subject to:

$$f(\dot{x}(t), x(t), u(t), \hat{\theta}, t) = 0,$$

$$\hat{y}(t) = h(x(t), \hat{\theta}, u(t)),$$

$$y^0 = \begin{cases} f(\dot{x}(t_0), x(t_0), u(t_0), \hat{\theta}, t_0) = 0, \\ \hat{y}(t_0) = h(x(t_0), \hat{\theta}, u(t_0)), \end{cases}$$

$$u^L \leq u(t) \leq u^u$$

$$x^L \leq x(t) \leq x^u \; \forall \, t \in [0, \tau]$$

The optimal iBIT test design vector, $\varphi_D$, of Eq. (7) may then applied to several fouling identification and isolation scenarios as described above and compared to iBIT effectiveness at nominal conditions.

The plate fin heat exchanger model may be formulated via a processor with the object-oriented language Modelica™, in the commercial software Dymola™. The model can be exported using the Functional Mockup Interface (FMI), a tool-independent standard for configuring dynamic models. A Functional Mockup Unit of the model may be exported, via a processor to a processing platform (e.g., MATLAB™) using a utility such as, for example, the Modelon FMI-Toolbox™. Dynamic and steady state parametric sensitivities may be calculated with the solver CVODES, a C-coded ODE solver capable of sensitivity analysis, using finite differences or adjoints. The optimal design may be calculated, with a processor, with the Mesh Adaptive Direct Search algorithm, NOMAD.

FIG. 2 shows Table 1, which shows estimated values and 95% confidence intervals of mass flow rates and thermal fouling resistance. The size, flow rates and Reynolds numbers of this heat exchanger are in much better agreement with those found in ECSs, whereas the experimental apparatus operates at a different regime, giving rise to considerably different sensitivities and dynamics for the heat transfer process. Here, we focus on the effectiveness of the methodology presented, rather than absolute values for the conditions estimated. The effectiveness of the proposed iBIT method is shown in some examples where the heat exchanger model presented above is studied under heavy foulant accumulation conditions. This may be accomplished by running the heat exchanger and the fouling models for 7 hours (real process time) with a high inlet foulant concentration of 100 mg/m$^3$ until the overall thermal fouling resistance reaches $6.2 \times 10^{-3}$ m$^2$ K/W. At this point, it is postulated that fouling is significant and may be identified from an iBIT, which is ran at nominal and optimal conditions and the capability of the iBIT to identify fouling with certainty is explored. We thus have a model representing noisy responses of a heat exchanger at significant fouling conditions, referred to herein as a "virtual system" and a model with no noise in its predictions and void of any foulant deposition, referred to hereafter as a "system model." The responses of the virtual system are used in a computational framework for parameter estimation to estimate the thermal fouling resistance and uncertain inputs of the system model.

The flow conditions in the ECS heat exchanger can be set to nominal conditions typical for ECS heat exchanger operations. The bleed inlet temperature may be constrained between 100° C. and 250° C., assuming that it is controlled upstream, but with significant uncertainty. The inlet ram temperature may be set according to the international standard atmospheric values at ground level determined by the International Standard Aviation Organization.

To evaluate the robustness of the proposed method for fouling detection, the thermal fouling resistance and uncertain flow conditions can be estimated in several case studies and their 95% confidence intervals at nominal and optimal conditions are reported and compared. Measurement noise may be added to the heat exchanger model outputs to provide virtual experimental data for analysis. The measurement standard deviation of the system $\sigma_{rs}$ may be assigned zero-mean white measurement noise typical for each outlet (0.5° C. for outlet temperatures, and 100 Pa for outlet pressures). Thereafter, noiseless model simulations (from the system model) can be matched to the experimental data (from the virtual system) by adjusting $\hat{\xi}$, the estimated parameters and system uncertain inlets. The robustness of fouling detection may be then determined as the capability of the parameter estimation to minimize deviations between the noiseless simulations of a model with zero initial fouling and noisy model responses of the model with heat exchanger fouling:

$$\min_{\hat{\xi}} \sum_{i=1}^{N_{sp}} \left( (T_{c,o,sim}^i - T_{c,o,exp}^i)^2 + (T_{h,o,sim}^i - T_{h,o,exp}^i)^2 \right) \quad (8)$$

$$0.75\bar{\xi} \leq \hat{\xi} \leq 1.25\bar{\xi}$$

Only temperature measurements can be compared for these studies, as it is more common to have temperature sensors available in ECS, and not pressure transducers. All uncertain inlet conditions can be subject to bounds that can be ±25% of their nominal value, $\bar{\xi}$.

As a first step we explored the robustness of the proposed method to identify heat exchanger fouling as a parametric fault in an ideal system with no uncertainty. Thus, the task here is to find optimal system conditions for estimating thermal fouling resistance, with all other system inputs known accurately. In the virtual system, thermal fouling resistance may be set to $6.2 \times 10^{-3}$ m$^2$ K/W, to represent realistic equilibrated fouling. For the optimal iBIT design, calculated by Eq. (7), the inlet temperature may be found at the upper bound of its allowable range (250° C.). Only one temperature step may be required ($n_s=1$) throughout the entire iBIT duration, r. Adding more input steps did not increase the estimation accuracy of fouling resistance in iBIT.

The fitting of the heat transfer resistance of the system model to the virtual system data produced thermal fouling resistance estimates of $6.26\pm0.40\times10^{-3}$ and $6.19\pm0.34\times10^{-3}$ m$^2$K/W at nominal and optimal conditions, respectively. In real systems, the inlet ram temperature depends on day time and location of the aircraft. The atmospheric conditions influence the rate of heat transfer, and therefore the fouling identifiability. To account for this, the thermal fouling resistance may be also estimated with inlet ram temperatures of −50° C. and 40° C. to represent cold and hot atmospheric conditions. The corresponding estimates of thermal fouling resistance can be nearly identical to the values listed for the standard inlet ram temperature. The estimated value of thermal fouling resistance and its confidence intervals can be slightly improved through optimal design of the iBIT inlet bleed temperature, regardless of the temperature of the atmosphere surrounding the aircraft.

One common uncertainty in ECS is the moisture of the ambient air. The aircraft surrounding atmosphere has different moisture levels depending on location, time, and the particular location in the airport. Therefore, it is of interest to consider uncertainty in the moisture content of air and explore its impact on the robustness of fouling identification using nominal and iBIT optimal inlets. For simplicity, the moisture content may be considered to affect only the heat capacity of each fluid in the system. From psychrometric charts, the maximum atmospheric humidity at 15° C. is 1.2 wt %, or 0.012 kg water/kg air, assuming there is no precipitation, while the minimum atmospheric humidity is roughly 0.1 wt %. This variability corresponds to a heat capacity range of 1040 to 1078 J/kg s. Thus, the heat capacity of air may be treated as an unknown in the optimal iBIT problem, with range as indicated above.

The optimal iBIT may be found with two control actions ($n_s=2$), signifying that two very different temperatures are needed for the separation of the effects of unknown moisture and fouling thermal resistance, when only outlet temperature measurements are available. In an optimal iBIT design, the bleed temperature may be set initially to the lower bound for 20 s, and then can be set to the upper bound for the remaining test duration. This design improves the estimation precision for the advective and convective aspects of heat transfer, both of which are affected by the specific heat capacity. A transitional period between the nominal and optimal settings may be required in order to reach the optimum steady-state outlet temperature for the first control step. The estimates of moisture and fouling thermal resistance can be acquired using the entire transient response exhibited by the system from the second input step change.

Fitting of the thermal fouling resistance and moisture content to the steady state data at nominal conditions (t=0 to 300 s, e.g.,) may produce estimates of $5.90 \pm 8.71 \times 10^{-3}$ m$^2$K/W and $1.21 \pm 3.67$ wt %, respectively. At optimal iBIT conditions, according to one exemplary embodiment, the estimates for $R_f$ and $w_{H_2O}$ are at $6.03 \pm 0.81 \times 10^{-3}$ m$^2$K/W and $1.27 \pm 0.28$ wt %. At minimum humidity levels the confidence intervals of the parameter estimates from nominal and optimal iBIT designs may be similar, indicating that the optimal iBITs are useful for estimating fouling regardless of the humidity levels. The 95% confidence region is notably large for the nominal design, to the degree that negative values for thermal fouling resistance and moisture content are deemed statistically feasible. Fouling estimation at uncertain moisture levels may be ineffective at the default settings, emphasizing the importance of applying a structured iBIT design strategy to improve the confidence and precision of fouling detection and isolation.

Figure 3:
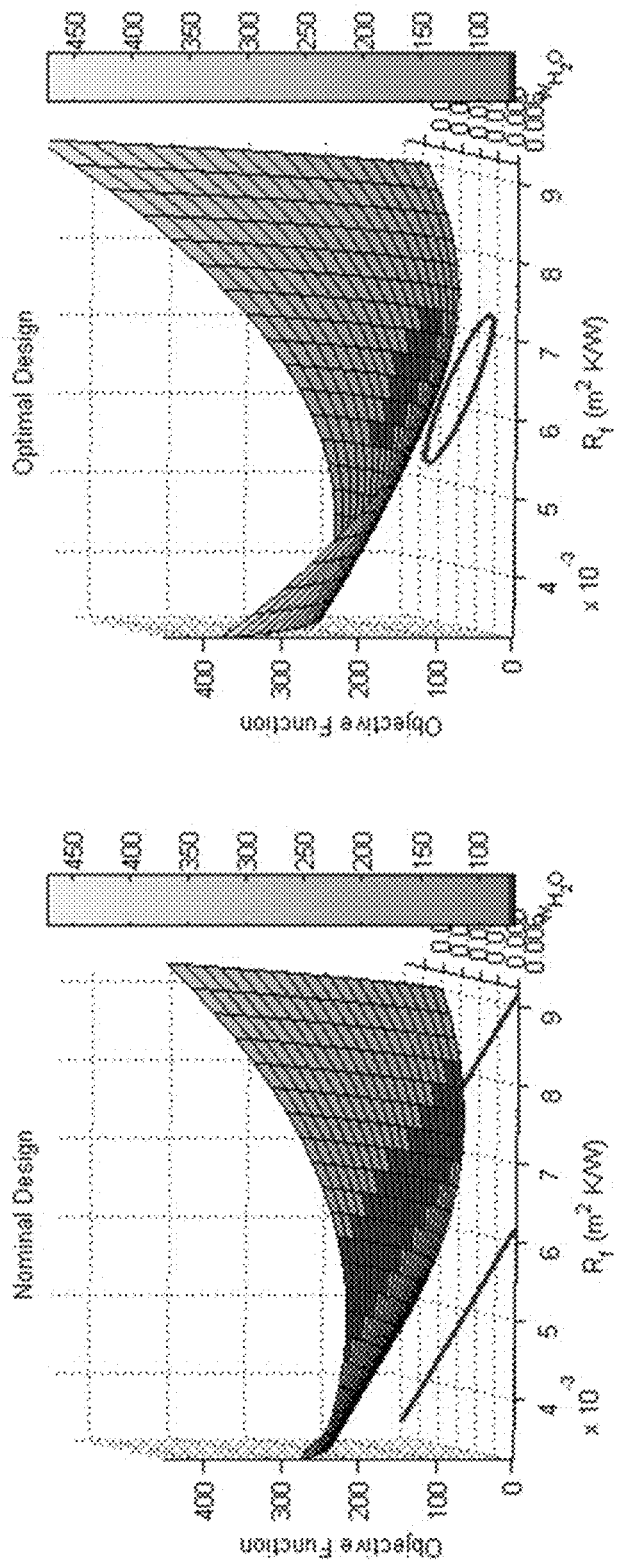
FIG. 3 depicts graphs of objective function values of the parameter estimation problem over a range of system model thermal fouling resistance and moisture content values using nominal (left) and optimal (right) iBIT settings.

FIG. 3 depicts objective function values of the parameter estimation problem over a range of system model thermal fouling resistance and moisture content values using nominal (left) and optimal (right) iBIT settings. The true values of the virtual system can be at 6.2×10-3 m2 K/W and 1.2 wt %, respectively. The dark squares represent the estimated parameters that correspond to the correct system output (the minimum objective function), and the contour plot shows the 95% confidence ellipses. Some embodiments may provide the opportunity to enumerate the objective function of Eq. (8) over the entire allowable space of thermal fouling resistance and moisture content values. Therefore, we can visualize the benefits of the proposed methodology for iBIT in terms of the corresponding capability to determine the unknown and uncertain system variables and parameters. FIG. 3 shows how the objective function, used for parameter estimation and thus fouling identification, is affected by the system model moisture content and thermal fouling resistance at nominal and optimal iBIT settings. At nominal iBIT, the objective function presents a valley of similar values neighboring the true values of $R_f$ and $w_{H_2O}$. Thus, the corresponding parameter estimation problem is applied to a system that is not identifiable. The range of $R_f$ and $w_{H_2O}$ yielding closely neighboring estimates for the objective function of Eq. (8) is significantly reduced in the optimal iBIT, thus the likelihood that parameters are estimated at their true values is significantly improved.

In certain ECSs, the pressure and temperature of the inlet bleed stream are controlled by a compression system. Depending on the state of the compressors and downstream pressure impedance, the pressure of the inlet bleed stream in the ECS heat exchanger might contain significant uncertainty. Therefore, in this case study we explored the impact of uncertain inlet pressure for the bleed side on iBIT fouling detection. As an exercise, uncertainty may be also considered for the ram flow. The sensitivities obtained in this case study produced Fisher information matrices that can be nearly singular for all available input configurations. At constant mass flow, the velocity and density of the fluid are inversely proportional, so the inlet pressure may have little impact on the Reynolds number. At nominal ECS flow conditions, the system pressure does not affect the intrinsic fluid flow properties enough to provide useful information. No experimental evidence may be found to validate this finding, as most studies that examine heat exchanger pressure focus on pressure drop analysis. Nonetheless, this case study indicates that uncertainty in inlet pressure should not affect a model-based iBIT process of fouling identification.

Inefficient operation of the ECS compressors may lead to uncertain flow rates for the bleed stream of the ECS. Similarly, the ram flow is controlled by a fan and other upstream system components that might bring uncertainty to the mass flow rate of that side of the heat exchanger. Thus, here the ram and bleed mass flows may be considered uncertain during the iBIT for fouling estimation. Three iBITs can be conducted to explore the impact of uncertainty in the flow rates: the first and second tests focused on uncertain bleed side and ram side flows rates, respectively, and a third test analyzed uncertain bleed side and ram side flow rates simultaneously. The results of these case studies for nominal and optimal iBITs are presented in FIG. 4, Table 2, along with the design vector for the optimal iBIT. Similar to the case of uncertain medium heat capacity, the mass flow rate affects the convective and advective heat transfer of the system and, thus, the overall thermal effectiveness of the heat exchanger. The 95% confidence intervals for the estimates of all the uncertain system inputs can be obtained at nominal and optimal conditions as shown in FIG. 4, Table 2.

According to some embodiments, fouling identifiability may decrease when applying uncertain flow rates, as expressed by the lack of accuracy in the estimates at nominal conditions and their wide confidence intervals. As expected, the system flow rates can have a significant impact on fouling detection, due to their influence on the heat transfer effectiveness. Nonetheless, vast improvements are feasible according to some embodiments.

With multiple unknown/uncertain system parameters, inputs and states, the task of using iBIT to estimate system fouling becomes a large-scale multi-variable optimization problem. It is clearly evident from the previous analyses that when fouling, air moisture and flow rates are simultaneously unknown or uncertain there is little chance in identifying fouling at nominal conditions with only one steady state test. Thus, the task here is to optimize a number of tests determined by D-optimal experimental designs, which by definition seek to separate parametric correlations, within an assigned design space. To confirm the robustness of the iBIT design methodology proposed here, a case study may be explored, in which ram inlet temperature, ram flow rate, moisture content, and thermal fouling resistance are considered unknown or uncertain.

Table 2, as depicted in FIG. 4, shows estimated values and 95% confidence intervals of uncertain heat exchanger inlets and fouling at nominal and optimal settings, according to some embodiments. Both steady state and transient information are used for fouling detection and isolation. These conditions may provide the highest heat transfer rates and substantial system dynamic responses. The confidence intervals for the estimated conditions can be calculated at the nominal and optimal iBIT settings are shown. These results show the greatest improvement in estimating uncertain inputs and fouling levels, indicating that the iBIT benefits the most from optimizing conditions for fouling identification when there are multiple uncertainties present.

Referring now to FIG. 5, Table 3 shows estimated values and 95% confidence intervals of uncertain heat exchanger inlets and fouling at nominal and optimal settings, according to some embodiments.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments.

Figure 6:
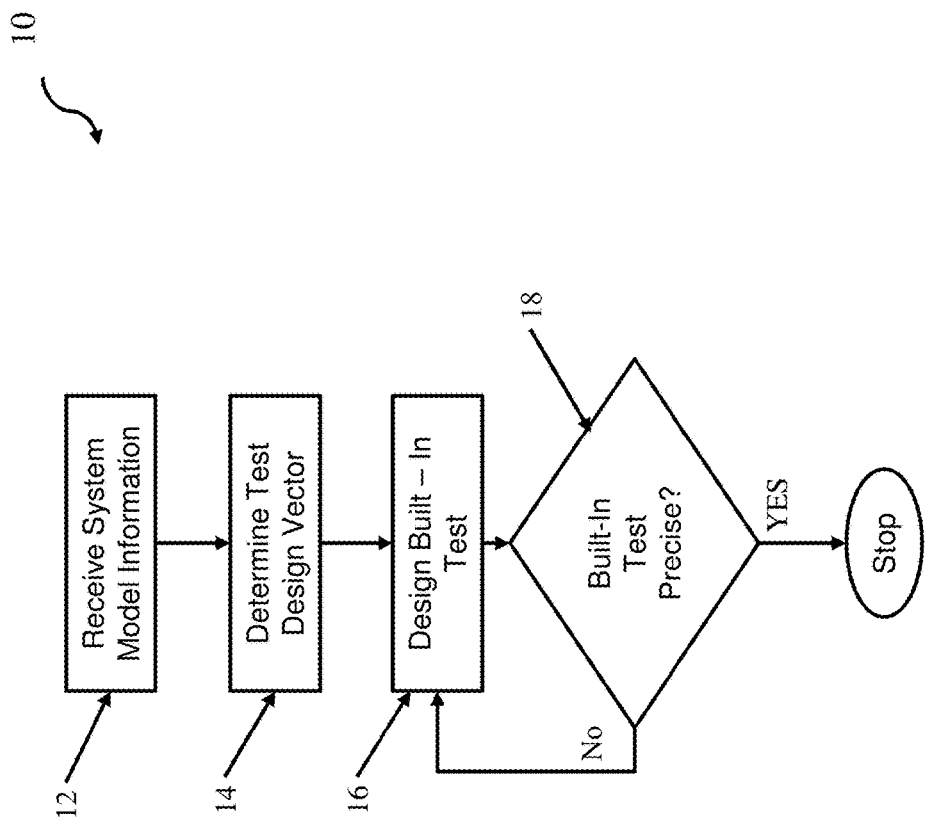
FIG. 6 depicts a flow diagram of a computer-implemented method for designing a built-in test, according to one embodiment.

FIG. 6 depicts a flow diagram 10 of a computer-implemented method for designing a built-in test, according to one embodiment. Referring briefly to FIG. 6, in some embodiments, a processor may be configured to receive subsystem model information from at least one sensor operatively connected to the processor, as shown in block 12. A subsystem model including system parameters for a heat exchanger, where each of the system parameters includes a sensor variance.

Figure 7:
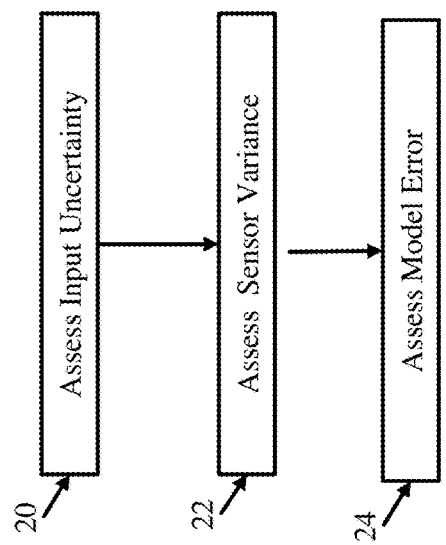
FIG. 7 depicts a method for designing a built-in test, according to one embodiment.

As shown in block 14, the processor may determine a test design vector based on one or more of the system parameters. FIG. 7 depicts a method 11 for designing a built-in test, according to one embodiment.

Referring now to FIG. 7, as shown in block 20, the processor may assess an input uncertainty. As shown in block 22, the processor may then assess the sensor variance for each of the system parameters received by the processor. At block 24, the processor may assess the model error. Determining the test design vector may include restricting an upper bound and a lower bound to each of the system parameters.

Referring again to FIG. 6, after determining the test design vector, the processor may design the built-in test based on the test design vector, as shown in block 16.

As shown in block 18, the processor may determine a precision value for the built-in test, compare the precision value for the built-in test with a predetermined precision threshold benchmark, and redesign a second built-in test responsive to determining that the precision value does not meet or exceed the predetermined precision threshold benchmark. For example, the precision threshold benchmark may be a nominal iBIT comprising a set of tests performed at normal or standard ECS conditions.

Figure 8:
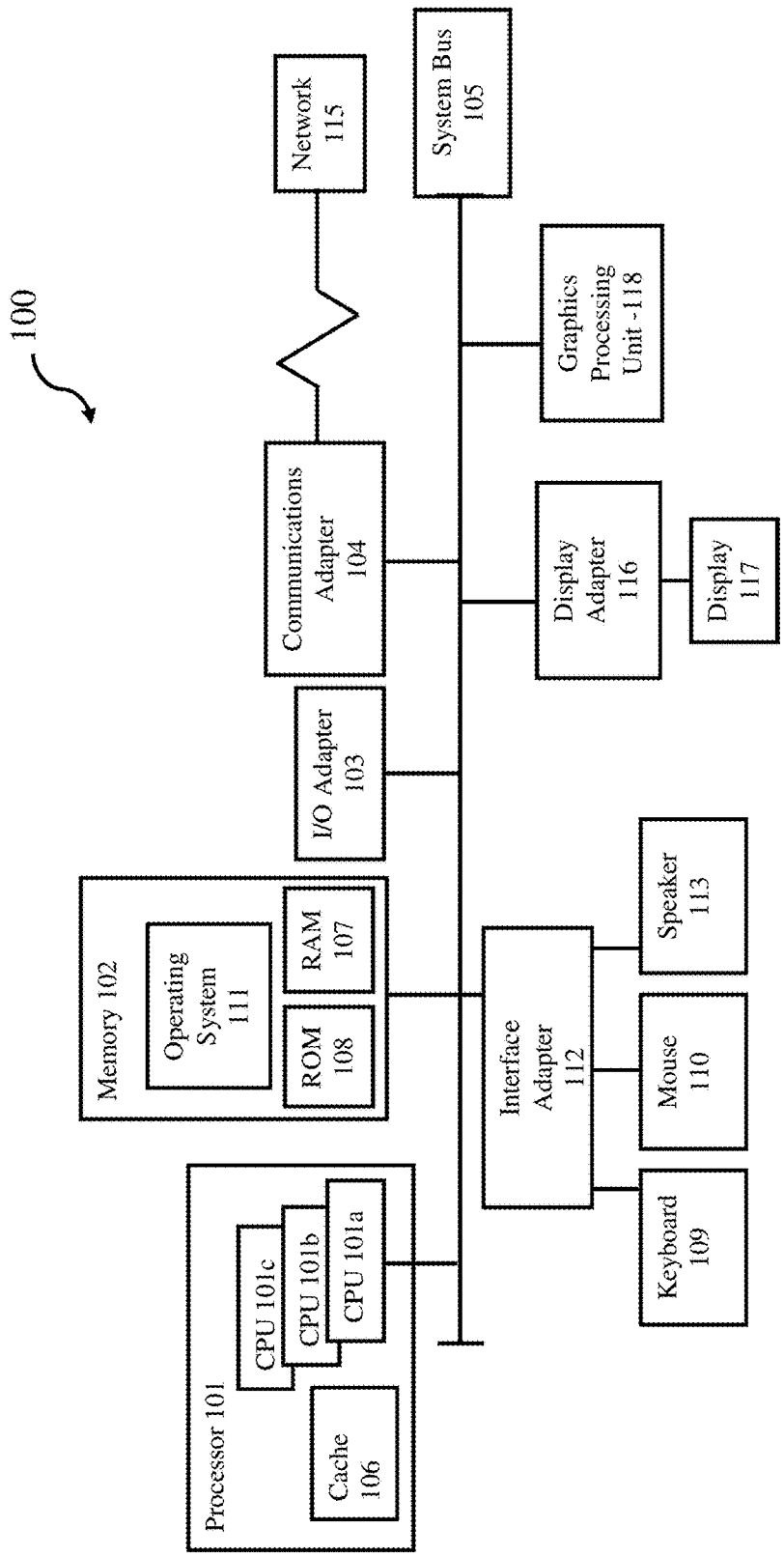
FIG. 8 depicts a block diagram of a computer system for use in practicing the teachings herein.

FIG. 8 illustrates a block diagram of a computer system 100 (hereafter "computer 100") for use in practicing the embodiments described herein. The methods described herein can be implemented in hardware, software (e.g., firmware), or a combination thereof. In an exemplary embodiment, the methods described herein are implemented in hardware, and may be part of the microprocessor of a special or general-purpose digital computer, such as a personal computer, workstation, minicomputer, or mainframe computer. Computer 100 therefore can embody a general-purpose computer. In another exemplary embodiment, the methods described herein are implemented as part of a mobile device, such as, for example, a mobile phone, a personal data assistant (PDA), a tablet computer, etc.

In an exemplary embodiment, in terms of hardware architecture, as shown in FIG. 8, the computer 100 includes processor 101. Computer 100 also includes memory 102 coupled to processor 101, and one or more input/output adaptors 103 that may be communicatively coupled via system bus 105. Memory 102 may be operatively coupled to one or more internal or external memory devices. Communications adaptor 104 may be operatively connect computer 100 to one or more networks 115. A system bus 105 may also connect one or more user interfaces via interface adaptor 112. Interface adaptor 112 may connect a plurality of user interfaces to computer 100 including, for example, keyboard 109, mouse 110, speaker 113, etc. System bus 105 may also connect display adaptor 116 and display 117 to processor 101. Processor 101 may also be operatively connected to graphical processing unit 118.

Processor 101 is a hardware device for executing hardware instructions or software, particularly that stored in a non-transitory computer-readable memory (e.g., memory 102). Processor 101 can be any custom made or commercially available processor, a central processing unit (CPU), a plurality of CPUs, for example, CPU 101a-101c, an auxiliary processor among several other processors associated with the computer 100, a semiconductor based microprocessor (in the form of a microchip or chip set), or generally any device for executing instructions. Processor 101 can include a memory cache 106, which may include, but is not limited to, an instruction cache to speed up executable instruction fetch, a data cache to speed up data fetch and store, and a translation lookaside buffer (TLB) used to speed up virtual-to-physical address translation for both executable instructions and data. Cache 106 may be organized as a hierarchy of more cache levels (L1, L2, etc.).

Memory 102 can include random access memory (RAM) 107 and read only memory (ROM) 108. RAM 107 can be any one or combination of volatile memory elements (e.g., DRAM, SRAM, SDRAM, etc.). ROM 108 can include any one or more nonvolatile memory elements (e.g., erasable programmable read only memory (EPROM), flash memory, electronically erasable programmable read only memory (EEPROM), programmable read only memory (PROM), tape, compact disc read only memory (CD-ROM), disk, cartridge, cassette or the like, etc.). Moreover, memory 102 may incorporate electronic, magnetic, optical, and/or other types of non-transitory computer-readable storage media. Note that the memory 102 can have a distributed architecture, where various components are situated remote from one another, but can be accessed by the processor 101.

The instructions in memory 102 may include one or more separate programs, each of which comprises an ordered listing of computer-executable instructions for implementing logical functions. In the example of FIG. 8, the instructions in memory 102 may include an operating system 111. Operating system 111 can control the execution of other computer programs and provides scheduling, input-output control, file and data management, memory management, and communication control and related services.

Input/output adaptor 103 can be, for example but not limited to, one or more buses or other wired or wireless connections, as is known in the art. Input/output adaptor 103 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

Interface adaptor 112 may be configured to operatively connect one or more input/output (I/O) devices to computer 100. For example, interface adaptor 112 may connect a keyboard 109 and mouse 110. Other output devices, e.g., speaker 113 may be operatively connected to interface adaptor 112. Other output devices may also be included, although not shown. For example, devices may include but are not limited to a printer, a scanner, microphone, and/or the like. Finally, the I/O devices connectable to interface adaptor 112 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like.

Computer 100 can further include display adaptor 116 coupled to one or more displays 117. In an exemplary embodiment, computer 100 can further include communications adaptor 104 for coupling to a network 115.

Network 115 can be an IP-based network for communication between computer 100 and any external device. Network 115 transmits and receives data between computer 100 and devices and/or systems external to computer 100. In an exemplary embodiment, network 115 can be a managed IP network administered by a service provider. Network 115 may be a network internal to an aircraft, such as, for example, an avionics network, etc. Network 115 may be implemented in a wireless fashion, e.g., using wireless protocols and technologies, such as WiFi, WiMax, etc. Network 115 may also be a wired network, e.g., an Ethernet network, an ARINC 429 network, a CAN, etc., having any wired connectivity including, e.g., an RS232 connection, R5422 connection, etc. Network 115 can also be a packet-switched network such as a local area network, wide area network, metropolitan area network, Internet network, or other similar type of network environment. The network 115 may be a fixed wireless network, a wireless local area network (LAN), a wireless wide area network (WAN) a personal area network (PAN), a virtual private network (VPN), intranet or other suitable network system.

If computer 100 is a PC, workstation, laptop, tablet computer and/or the like, the instructions in the memory 102 may further include a basic input output system (BIOS) (omitted for simplicity). The BIOS is a set of essential routines that initialize and test hardware at startup, start operating system 111, and support the transfer of data among the operatively connected hardware devices. The BIOS is stored in ROM 108 so that the BIOS can be executed when computer 100 is activated. When computer 100 is in operation, processor 101 may be configured to execute instructions stored within the memory 102, to communicate data to and from the memory 102, and to generally control operations of the computer 100 pursuant to the instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for designing and operating a built-in test (BIT) comprising:
   receiving, via a processor, a subsystem model for a heat exchanger, the model including system parameters for inputs for the heat exchanger, wherein each of the inputs is limited to variation between upper and lower bounds and can be measured by a sensor having a sensor variance;
   determining, via the processor, a test design vector based on one or more of the system parameters, wherein determining includes assessing an input uncertainty;
   assessing, via the processor, the sensor variance for each of the inputs;
   assessing, via the processor, a system model error;
   designing, via the processor, the built-in test based on the test design vector; and
   applying the BIT to an aircraft based on at least an inlet bleed temperature that the BIT causes the aircraft to increase by at least one discrete step during the test to determine fouling in the heat exchanger.

2. The computer-implemented method of claim 1, wherein the system parameters comprise a thermal fouling resistance, a moisture content, an inlet pressure and a mass flow.

3. The computer-implemented method of claim 1, further comprising:
   determining, via the processor, a precision value for the designed built-in test;
   comparing, via the processor, the precision value for the designed built-in test with a predetermined precision threshold benchmark; and
   redesigning, via the processor, a second built-in test responsive to determining that the precision value does not meet or exceed the predetermined precision threshold benchmark.

4. The computer-implemented method of claim 3, wherein redesigning the second built-in test comprises altering, via the processor, at least one sensor variance.

5. A computer program product for designing and operating a built-in test (BIT), the computer program product comprising a computer readable storage medium having program instructions embodied therewith, wherein the computer readable storage medium is not a transitory signal per se, the program instructions executable by a processor operatively connected to at least one sensor to cause the processor to perform a method comprising:
   receiving, via the processor, a subsystem model for a heat exchanger, the model including system parameters for inputs for the heat exchanger, wherein each of the inputs is limited to variation between upper and lower bounds and can be measured by a sensor having a sensor variance;
   determining, via the processor, a test design vector based on one or more of the system parameters, wherein determining includes assessing an input uncertainty;
   assessing, via the processor, the sensor variance for each of the inputs;
   assessing, via the processor, a system model error;
   designing, via the processor, the built-in test based on the test design vector; and
   applying the BIT to an aircraft based on at least an inlet bleed temperature that the BIT causes the aircraft to increase by at least one discrete step during the test to determine fouling in the heat exchanger.

6. The computer program product of claim 5, wherein the system parameters comprise a thermal fouling resistance, a moisture content, an inlet pressure and a mass flow.

7. The computer program product of claim 5, further comprising
   determining, via the processor, a precision value for the built-in test;
   comparing, via the processor, the precision value for the built-in test with a predetermined precision threshold benchmark; and
   redesigning, via the processor, a second built-in test responsive to determining that the precision value does not meet or exceed the predetermined precision threshold benchmark.

8. The computer program product of claim 7, wherein redesigning the second built-in test comprises altering, via the processor, at least one sensor variance.

9. A computer-implemented method for designing and operating a built-in test (BIT) comprising:
- receiving, via a processor, a subsystem model for a heat exchanger, the model including system parameters for inputs for the heat exchanger, wherein each of the inputs is limited to variation between upper and lower bounds and can be measured by a sensor having a sensor variance;
- determining, via the processor, a test design vector based on one or more of the system parameters, wherein determining includes assessing an input uncertainty and assessing, via the processor, the sensor variance for each of the inputs;
- designing, via the processor, the built-in test based on the test design vector; and
- applying the BIT to an aircraft based on at least an inlet bleed temperature that the BIT causes the aircraft to increase by at least one discrete step during the test to determine fouling in the heat exchanger.

* * * * *